United States Patent [19]

Zeikus et al.

[11] 4,425,432
[45] Jan. 10, 1984

[54] PROPAGATION OF MICROBIAL CELLS ON SINGLE CARBON PRODUCTS

[75] Inventors: Joseph G. Zeikus; Lee H. Lynd, both of Madison, Wis.

[73] Assignee: Wisconsin Alumini Research Foundation, Madison, Wis.

[21] Appl. No.: 286,246

[22] Filed: Jul. 23, 1981

[51] Int. Cl.$^3$ ............... C12P 7/54; C12P 7/52; C12N 1/20; C12R 1/01
[52] U.S. Cl. ................ 435/140; 435/141; 435/247; 435/253; 435/822
[58] Field of Search ............... 435/140, 141, 253, 822, 435/247

[56] References Cited

U.S. PATENT DOCUMENTS 4,106,988  8/1978  Ohsugi et al. ............... 195/49

OTHER PUBLICATIONS

J. G. Zeikus, et al., Current Microbiology, vol. 3, pp. 381–386, 1980.
American Type Culture Collection Catalogue of Strains I, Fifteenth Edition, p. 92, 1982.
P. J. Weimer and J. G. Zeikus, Arch. Microbiol., vol. 119, pp. 49–57, 1978.
Zeikus et al., Arch. Microbiol. 122, 41–48 (1979).

*Primary Examiner*—Robert J. Warden
*Attorney, Agent, or Firm*—Quarles & Brady

[57] ABSTRACT

A process for the propagation of microbial cells and the production of fermentation products, such as acetic and butyric acid, comprises anaerobically growing an acidogenic bacterium, such as a strain of *Butyribacterium methylotrophicum* ATCC 33226, in a nutrient medium containing a single carbon product, such as methanol, as the fermentation substrate or main source of assimilable carbon, accumulating the microbial cells in said medium and then separating and recovering said microbial cells and desired fermentation products from the spent media.

13 Claims, 4 Drawing Figures

PROPAGATION OF MICROBIAL CELLS ON SINGLE CARBON PRODUCTS

The U.S. Government has rights to this invention pursuant to Grant No. DEB-7824071 and IPA No. 0001 awarded by the National Science Foundation.

FIELD OF THE INVENTION

The present invention relates to a process for the propagation of microbial cells and is more specifically directed to a process for propagation of microbial cells and the production of acids, such as acetic or butyric acid, by anaerobically culturing an acidogenic bacterium in a medium containing a single carbon product such as methanol or carbon monoxide as the fermentation substrate or main source of assimilable carbon.

BACKGROUND OF THE INVENTION

The propagation of microbial cells to obtain either fermentation products or to recover cell protein or both is well known. Furthermore, processes for the propagation of microbial cells in a medium containing hydrocarbons as the main assimilable carbon source are also known.

There is considerable interest in fermentation processes which can use as the fermentation substrate simple hydrocarbons and other inexpensive carbonaceous materials, such as methanol, synthesis gas ($H_2$ and CO), or a mixture of $CO_2$ and $H_2$ which would normally be flared or otherwise disposed of in petroleum refining.

The use of methanol as the main source of assimilable carbon in such fermentation processes is particularly attractive because of the advantages it offers. Methanol has the advantage of being miscible with water; it can be easily and cheaply produced from a wide range of hydrocarbon materials; it can be easily produced in virtually any area of the world having any form of fossil fuel supplies and it is characterized by the absence of potentially carcinogenic polycyclic hydrocarbons.

In the past, attempts to grow microbial cells using methanol as the main assimilable carbon source have not been particularly successful. The ability of microorganisms to grow on single carbon compounds, especially those that contain methyl groups, appears restricted to a specialized metabolic group known as methylotrophs. By and large, most of what is known about methyltrophic bacteria is limited to obligately aerobic species that generally contain novel pathways foe one-carbon metabolism (1). More recently, studies on one-carbon metabolism in anaerobic methanogens have demonstrated that these bacteria can grow on either $CH_3OH$, $H_2/CO_2$, CO, or methylamine as sole sources of carbon and energy (2, 3, 4, 5). Several species of anaerobic acidogenic bacteria have been described that can grow on $H_2/CO_2$ or formate as sole carbon and energy sources (6,7) or that contain unique one-carbon metabolism reactions for homoacetic acid fermentations of multicarbon compounds (8,9).

In the past, *Methanosarcina barkeri* was the only described obligately anaerobic bacterium known to be capable of utilizing methanol and other one carbon compounds as the sole source of energy for growth.

The development of a process for the biological conversion of coal or biomass pyrolysis products (e.g. $H_2$, $CO_2$, CO and $CH_3OH$) to multicarbon atoms would be valuable as it would allow the further development of processes for chemical feed stock production.

SUMMARY OF THE INVENTION

It is an object of the present invention is to provide an anaerobic process for propagation of microbial cells with high vitamin and protein value on single carbon products to provide microbial cells and valuable fermentation products.

It is a further object to disclose our discovery that anaerobic, acidogenic microorganisms can be grown on single carbon products to produce higher carbon products such as acetic acid and butyric acid.

In the method of the present invention an acidogenic microorganism, such as *Butyribacterium methylotrophicum*, is anaerobically grown in a medium containing a single carbon product such as methanol, CO or synthesis gas to obtain microbial cells, and acids such as acetic and butyric acids.

The preferred acidogenic microorganism is *Butyribacterium methylotrophicum* which is a methylotrophic, acidogenic, anaerobic bacterium that was first isolated from a sewage digestor in Marburg, Federal Republic of Germany.

The neotype strain of the species is a pure culture of the Marburg strain which has been deposited in the American Type Culture Collection (Rockville, Md) accession number ATCC 33266. It is a mesophilic, Gram-positive, nonmotile, pleomorphic rod that perfoms homoacetic, homobutyric, or heteroacidic fermentations. Cell morphology varies from single or paired straight rods to rudimentarily branched rods, club-shaped cells, or oval refractile cells. Cell heat resistance correlated with the presence of a few refractile cells. Electron micrographs of thin sections revealed a thick monolayered cell wall and an atypical spore structure. The DNA base composition was $48.8 \pm 0.2$ mol% guanosine plus cytosine. Corrinoid levels varied from $0.35 \pm 0.16$ to $7.9 \pm 1.6$ µg/mg cell dry weight when cells were grown on glucose or methanol/acetate/$CO_2$ respectively. Batch growth in a mineral medium that contained 0.1% yeast extract, $N_2/CO_2$, 100 mM methanol, and 50 mM Na acetate displayed a 20 h doubling time, final $A_{540}$ of 0.9, butyric acid yield of 25 mM, and ~stoichiometry of 3 mol butyrate formed per 10 mol methanol and 2 mol $CO_2$ fermented. The isolation and characterization of the Marburg strain is described in detail by Zeikus et al in *Current Microbiology*, Vol. 3 (1980) pp. 381-386 which is incorporated by reference herein.

Until definitive evidence becomes available, *Butyribacterium methylotrophicum* should be placed in the family Propionibacteriaceae. Barker (10) first described the genus Butyribacterium and the species *B. rettgeri*. This species was a Gram-positive nonmotile rod that displayed the same acid fermentation of glucose and lactate as the Marburg strain. However, *B. rettgeri* is now recognized as *Eubacterium limosum* (11).

The propagation of an acidogenic bacterium, such as *Butyribacterium methylotrophicum*, in a single carbon product as its main source of carbon and energy can provide high quality, low cost microbial protein, vitamins and enzymes as well as a means of transforming coal pyrolysis or synthesis gas mixtures or simple one carbon compounds such as CO, $CO_2$ or $CH_3OH$ into more valuable larger molecular weight compounds such as acetic acid and butyric acid.

DESCRIPTION OF THE PREFERRED EMBODIMENT

Figure 1:
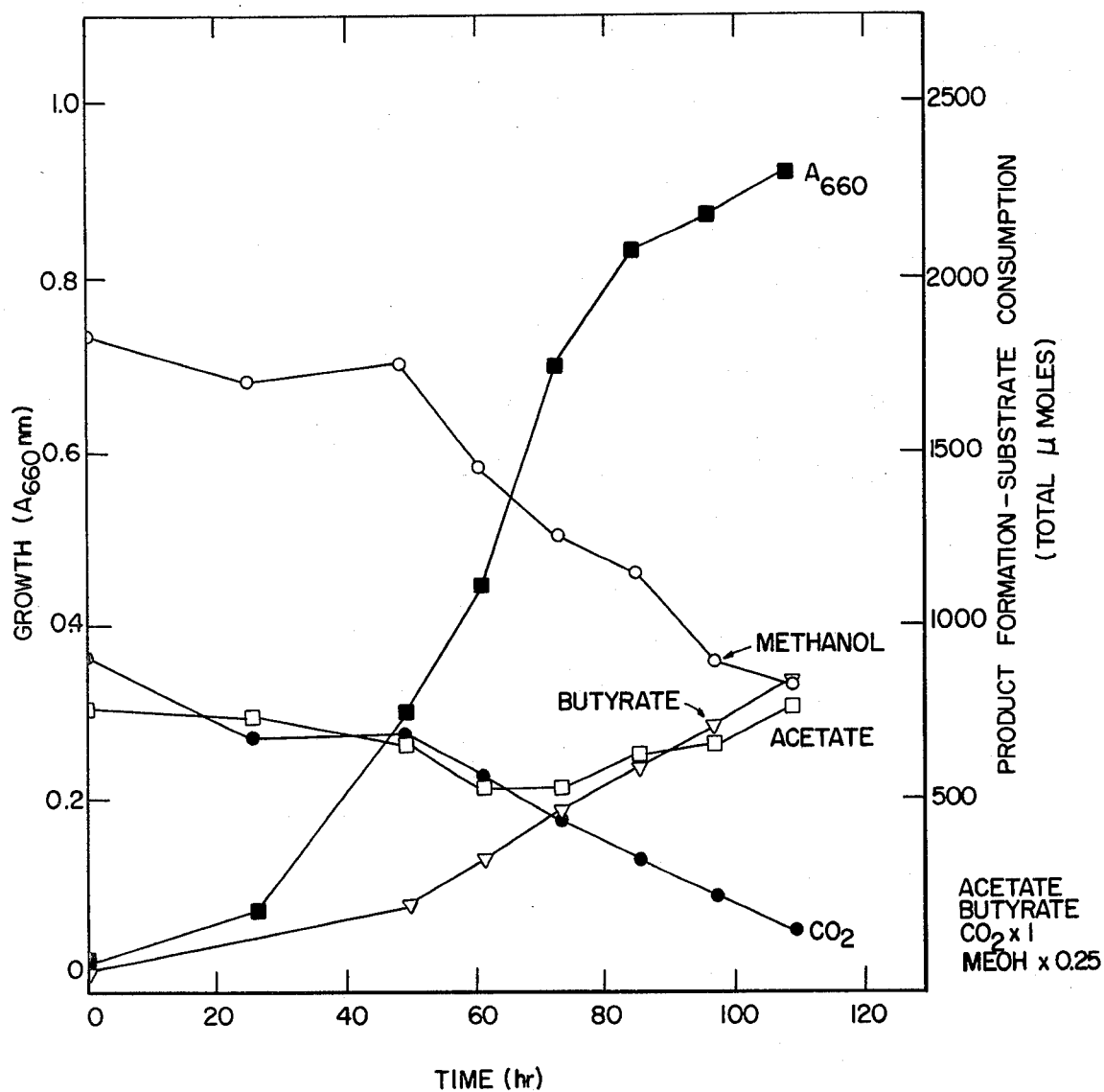
FIG. 1 shows the fermentation parameters of *B. methylotrophicum* on methanol/acetate and $CO_2$.

In the preferred practice of the present invention a methanol utilizing acidogenic microorganism, preferably *Butyribacterium methylotrophicum*, is grown under anaerobic conditions in a culture medium which in addition to essential vitamins and minerals contains a single carbon product as the main assimilable carbon and energy source.

When *B. methylotrophicum* is the microorganism the growth medium is supplemented with yeast extract or a growth factor (less than 0.2% of media) and maximum cell growth is obtained when the media also contains a high concentration of acetate (at least 0.1%).

The choice of the single carbon product which serves as the main assimilable carbon source to be used depends upon the selection of the organism and may determine the fermentation products produced. For example, when *B. methylotrophicum* is the organism and the carbon source is CO the products recovered are cells and acetic acid; if the carbon source is a mixture of $CO_2$, acetate and methanol the products recovered are cells and butyric acid; if the carbon source is methanol in a CO atmosphere the products recovered are cells and acetic acid; if the carbon source is a mixture of $CO_2$ and $H_2$ the products recovered are cells and acetic acid; and, if the carbon source is CO and $H_2$ the recovered products are cells and acetic acid.

The practice of the present invention is further illustrated by the experimental work which is described below.

EXPERIMENTAL MATERIALS AND METHODS

Culture techniques

Media preparation and enrichment-isolation and growth of the organism employed cultural techniques described in the literature for obligate anaerobes (12,13). The LPBB medium used was a phosphate-buffered mineral salts medium containing the following ingredients per liter of distilled water:

$NH_4Cl$, 0.9 G; NaCl, 0.9 g; $MgCl_2$, 0.2 g; $KH_2PO_4$, 0.75 g; $K_2HPO_4$, 1.5 g; trace mineral solution, 9 ml; 10% $FeSO_4$, 0.03 ml; 0.2% resazurin, 1 ml; vitamin solution, 5 ml; and 10 ml of 10% $Na_2S$ which was added before autoclaving. The trace mineral solution contained per liter distilled $H_2O$:12.8 g nitrilotriacetic acid neutralized to pH 6.5 with KOH, $FeCl_3 \times 4H_2O$, 0.2 g; $MnCl_2.4H_2O$, 0.1 g; $CoCl_2.6H_2O$, 0.17 g; $CaCl_2.2H_2O$, 0.1 g; $ZnCl_2$, 0.1 g; $CuCl_2$, 0.02 g; $H_3BO_3$, 0.01 g; $NaMoO_4.2H_2O$, 0.01 g; NaCl, 1.0; and $Na_2SeO_3$, 0.02 g.

(12) The gas phase in all anaerobic culture tubes was $N_2/CO_2(95:5)$ unless otherwise specified. The LPBB medium was supplemented with 0.05% yeast extract and, where indicated, various additions. Additions (e.g., energy sources) were sterilized separately and then added to yeast extract-supplemented LPBB medium. Growth inhibitors and antibiotics were not autoclaved before addition. The TYEG medium consisted of LPBB medium supplemented with 0.3% yeast extract, 1.0% tryptone, and 0.5% glucose. The CBBM medium was the carbonate buffered medium described by Zeikus and Wolfe (5). The pH of all culture media was 7.4–7.5. Cells used for growth, nutritional, and morphological studies were cultured in 23-ml anaerobic culture tubes (18 × 142 mm) from Bellco (Vineland, N.J.) which contained 10 ml of medium and were sealed with no. 2 black butyl stoppers (Scientific Products, McGraw Park, Ill.). Cells were routinely mass-cultured in 18-liter glass carboys (Wheaton Scientific, Millville, N.J.) that were sealed with butyl rubber stoppers and contained a $N_2/CO_2(95:5)$ gas phase. Cells used for DNA base composition determination were cultured at 37° C. in 12 liters of TYEG medium. When an $OD_{660}$ of 0.4 was obtained, penicillin G (Sigma Chemical Co., St. Louis, Mo.) was added to a final concentration of 100 g/ml and the culture was incubated for an additional 12 h before harvesting.

Enrichment cultures employed a 1-ml inoculum of either sewage sludge obtained from anaerobic digestors in Marburg, West Germany, in August, 1976, and Madison, Wis., in 1977–1980, or sediment slurry from Lake Mendota in August, 1978. Enrichment cultures used LPBB medium supplemented with 0.05% yeast extract, 100 mM methanol, and 50 mM potassium acetate. Enrichment cultures were repeatedly transferred in the above medium, and the culture was purified by picking individual colonies from agar (1.5%) streak plates of the same medium in an anaerobic chamber (Coy Laboratory Products, Ann Arbor, Mich.) and subsequent transfer to anaerobic culture tubes. Stock cultures can be stored anaerobically at 18°, 4°, −20°, or −80° C. and remain viable for many months.

Growth characterization

Growth was determined by measuring the increase in turbidity at 540 or 660 nm. Optical density was quantified directly by insertion of the anaerobic culture tubes into a Spectronic 20 (Bausch and Lomb, Rochester, N.Y.) spectrophotometer. All growth-fermentation experiments employed duplicate tubes, and the results represent mean values. All individual experiments were duplicated or triplicated. Metabolic gases, alcohols, and fatty acids were quantified by the gas chromatographic procedures described by Nelson and Zeikus (14) and Zeikus, Hegge, and Anderson (12).

Cellular characterization

A Carl Zeiss photomicroscope was used for phase-contrast observations including determination of cell size. The methods used for preparing cells for thin sectioning and electron microscopic examination were as described by Zeikus and Bowen (15). However, two different fixation methods were employed: the glutaraldehyde-osmium tetroxide procedures as described previously (15) and a modified procedure in which 0.05% final concentration ruthenium red was added to the cacodylate buffer and both the glutaraldehyde and osmium tetroxide fixatives.

DNA was isolated and purified from lysozyme-treated cells by the method of Marmur (16). DNA base compositions were determined by both thermal denaturation and buoyant density centrifugation. Thermal denaturation employed the method of De Ley (17); base compositions were calculated from melting profiles obtained with 0.1× standard saline citrate solution in a Gilford model 250 spectrophotometer equipped with a model 2527 thermoprogrammer. *Escherichia coli* DNA VIII, lot no. 57C-6830 from Sigma served as standard and displayed a mol% G+C of 52.8 (±2). Buoyant density centrifugation employed the method of Wells and Blair (18); *Agrobacterium tumefaciens* strain C58 DNA (density 1.718) was the standard. Identical values of DNA G+C content (±0.4%) were obtained by both procedures. Results represent the average of three separate determinations.

Corrinoids in cells were quantified by a bioassay utilizing *Escherichia coli* 113-3 and procedures described by Krzycki and Zeikus (19).

Results

Successful enrichment required a medium that contained mineral salts, methanol, and acetate. *Butyribacterium methylotrophicum* strains obtained from sewage sludge and lake sediment in Madison appeared similar to the Marburg strain in morphology and general growth features. The Marburg strain was characterized in detail and is the type strain of this species.

*B. methylotrophicum* formed uniformly round, mucoid, pink-pigmented colonies that varied in diameter from 1.0 to 3.0 mm. Cells grown to the midexponential phase in methanolacetate medium existed singly or in pairs and often displayed rudimentary branching. The average size of single cells was 0.8±0.2 µm in width and 2.7±0.54 µm in length. Cell pleomorphism observed in stationary phase and older cultures included branched, club-shaped, and refractile cells. Cell resistance to heating at 80° C. for 10 min. was detected in older cultures (2 weeks or older) that contained a few refractile endospore-like structures. The formation of refractile cells and spores was stimulated by the addition of soil extract or by limiting phosphate in the culture medium. *B. methylotrophicum* was Gram positive and motility was not observed in wet mounts. Electron microscopic observations of thin sections revealed that cells had a typical Gram-positive cell wall architecture and an outer envelope surface that was stained by ruthenium red. Most notably the vegetative cell was was often thickened at cell ends and the spore structure appeared as one thick coat layer surrounding the spore cytoplasm without visible cortex and exosporium layers.

DNA isolated from the Marburg strain had a base composition of 49.8±0.2 mol% G+C. Late stationary phase cells grown on methanol often appeared light red. Examination of corrinoid levels in cells grown in TYEG medium and in the same medium but with methanol instead of glucose as energy source revealed 0.35±1.6 and 7.9±1.6 µg corrinoids per mg cell dry weight, respectively. Catalase was not detectable. The sensitivity of various antibiotics and inhibitors on growth of the Marburg strain and *Clostridium pasteurianum* was compared (Table 1). *B. methylotrophicum* was sensitive to antibiotics that inhibit cell wall synthesis and ribosome function. The Marburg strain was noticeably more tolerant of sodium azide and sodium chloride than was *C. pasteurianum*. Oxygen was an effective inhibitor of growth.

Growth of the Marburg strain requires cofactors in yeast extract (0.05% final concentration) that can not be replaced by a vitamin mixture (5). *B. methylotrophicum* grew ($\Delta A_{660} \geq 0.2$ after 6 days at 37° C.) on LPBB medium, 0.05% yeast extract, and one of the following energy sources: lactate (0.5%), pyruvate (0.5%), glucose (0.5%), sucrose (0.5%), glycerol (0.5%), fructose (0.5%), $H_2/CO_2$(1 atm), and $CH_3OH$ (100 mM). Growth was not detectable on formate, ethanol/acetate, or acetate as energy sources. The optimum temperature for growth was 37°–40° C., the maximum was less than 50° C., and the minimum was greater than 10° C. The pH optimum for growth of the Marburg strain was about 7.5. No growth occurred when the initial pH was below 6 or above 9.

The acid products formed by *B. methylotrophicum* on different energy sources are compared in Table 2. A mixture of acetic and butyric acids are formed with glucose, methanol, and other energy sources examined other than $H_2/CO_2$ or $CO_2/CH_3OH$/acetate. The only acid product formed on $H_2/CO_2$ was acetic, and butyric acid was the only detectable product on $CO_2/CH_3OH$/acetate. Formic acid was not detected as a fermentation product. The relationship between methanol consumption, butyrate formation and growth of the Marburg strain on $CO_2/CH_3OH$/acetate medium is shown in FIG. 1. The doubling time under these conditions was ~20 h. The acetate concentration did not change significantly during the time course and $H_2$ was not detected as an end product. A stoichiometry of 3 mol butyrate formed per 10 mol methanol fermented was observed. $CO_2$ accounts for the carbon in butyrate not supplied from methanol. Cell densities of greater than 2.8 ($A_{660}$) have been observed in $CH_3OH$/acetate medium that contains high yeast extract (0.3%) and non-limiting methanol. A doubling time of under 2 hrs. was observed in methanol limited chemostat cultures.

TABLE 1

Effect of antibiotics and inhibitors on growth of the Marburg strain.

| | % Inhibition of growth[b] | |
|---|---|---|
| Agent[a] | Marburg strain | *Clostridium pasteurianum* |
| Penicillin | 100 | 100 |
| Streptomycin | 80 | 100 |
| Tetracycline | 100 | 100 |
| Chloramphenicol | 100 | 100 |
| Sodium azide | | |
| 50 µg/ml | 0 | 100 |
| 250 µg/ml | 0 | 93 |
| Sodium chloride (2%) | 0 | 73 |
| Oxygen[c] | 100 | 100 |

[a]Final concentration, unless indicated, was 100 µg/ml.
[b]Growth in TYEG medium ± agent was determined after 8 days and 10 h incubation for the Marburg strain and *C. pasteurianum*, respectively; 0% inhibition of growth represents a final $A_{540}$ of 1.2–0.95 for the cultures examined.
[c]Culture was incubated aerobically in a shake flask sealed with a cotton stopper.

TABLE 2

Relationship between growth and acid production by the Marburg strain.[a]

| | Growth | Acid products ($\Delta mM$) | | Final |
|---|---|---|---|---|
| Energy source | ($\Delta A_{540}$) | Acetic | Butyric | pH |
| Glucose | 1.20 | 31 | 8 | 5.1 |
| $CH_3OH$/acetate | 1.10 | ND | 30 | 6.7 |
| $H_2/CO_2$ | 0.19 | 19 | 0 | 5.5 |
| $CH_3OH$ | 0.31 | 3 | 6 | 7.2 |
| None | 0.06 | 1 | 2 | 7.5 |

[a]Experimental tubes contained: LPBB medium, 0.1% yeast extract, 1 atm $N_2/CO_2$ (95:5) except for $H_2/CO_2$ (80:20) tubes, and either 0.5% glucose, 100 mM $CH_3OH$/50 mM Na acetate, 1 atm $H_2/CO_2$, or 100 mM $CH_3OH$, as indicated. A 5% inoculum grown on methanol/acetate was used to initiate cultures that were incubated at 37° C. for 6 days. ND: not detectable.

The practice of the invention is further illustrated by the following examples.

EXAMPLE 1

Fermentation of *B. Methylotrophicum* on Methanol/Acetate $CO_2$

The *B. methylotrophicum* was grown in 158 ml pressure bottles containing 80 ml of phosphate-buffered mineral medium with 0.05% yeast extract, methanol and acetate in an $N_2/CO_2$ gas phase at an incubation temperature of 37° C. The fermentation parameters of *B. methylotrophicum* during growth under these conditions is shown in FIG. 1.

EXAMPLE 2

Fermentation of *B. Methylotrophicum* Adapted to Grow on 100% CO

A variant of *B. methylotrophicum* was adapted to grow on CO alone by transfer of the Marburg strain into a medium with methanol/acetate/$CO_2$ and a 30% CO gas phase; transfer of that culture into the same medium with a 100% CO gas phase; and 4 successive transfers on 100% CO.

Figure 2:
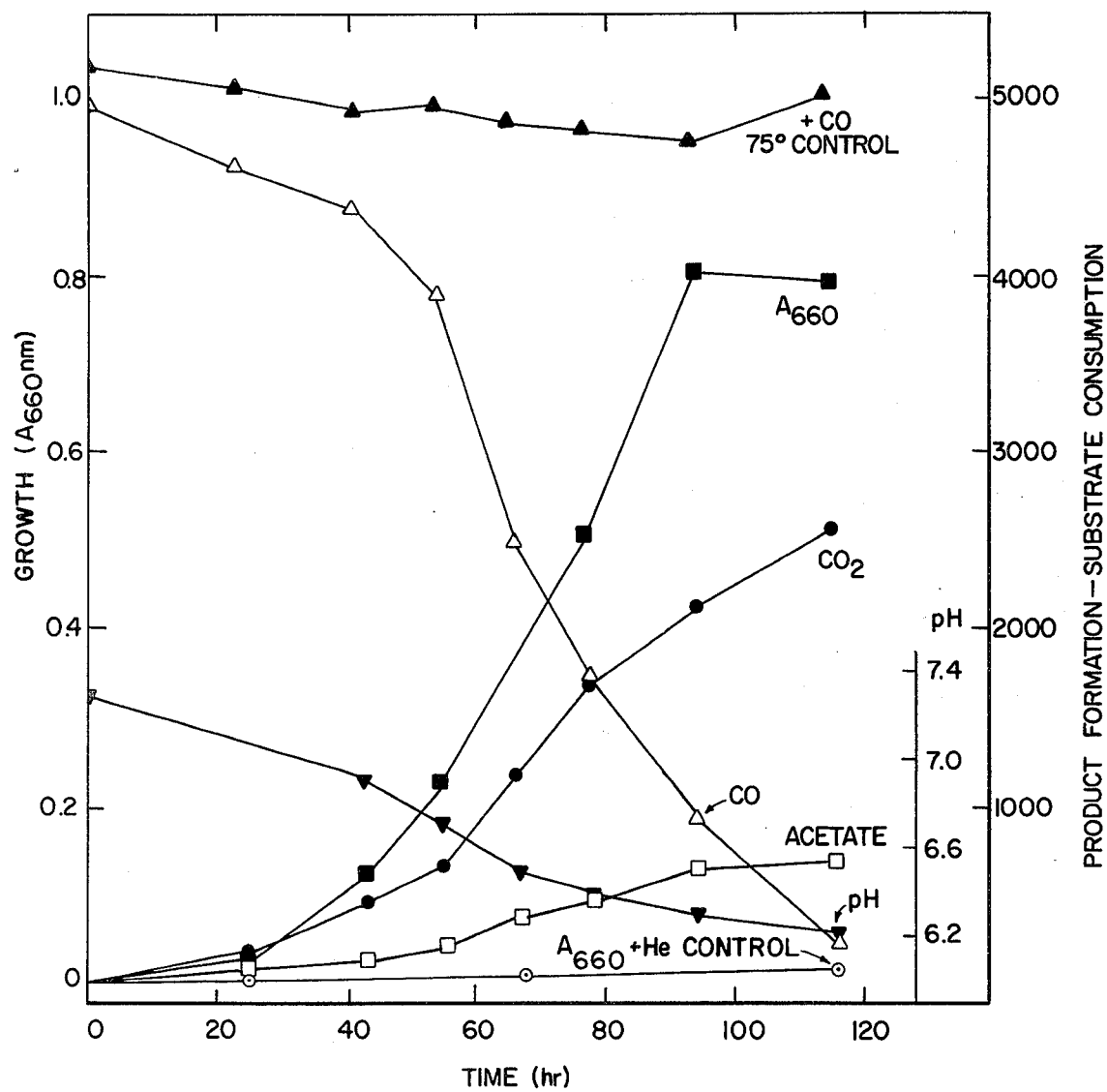
FIG. 2 shows the fermentation parameters of the *B. methylotrophicum* mutant adapted to grow on 100% CO.

The resulting pure culture was grown in 158 ml. pressure bottles containing 52 ml. of phosphate buffered mineral medium with 0.05% yeast extract, and a 100% gas phase at an incubation temperature of 37° C. The fermentation parameters of the culture growth under these conditions is shown in FIG. 2.

EXAMPLE 3

Figure 3:
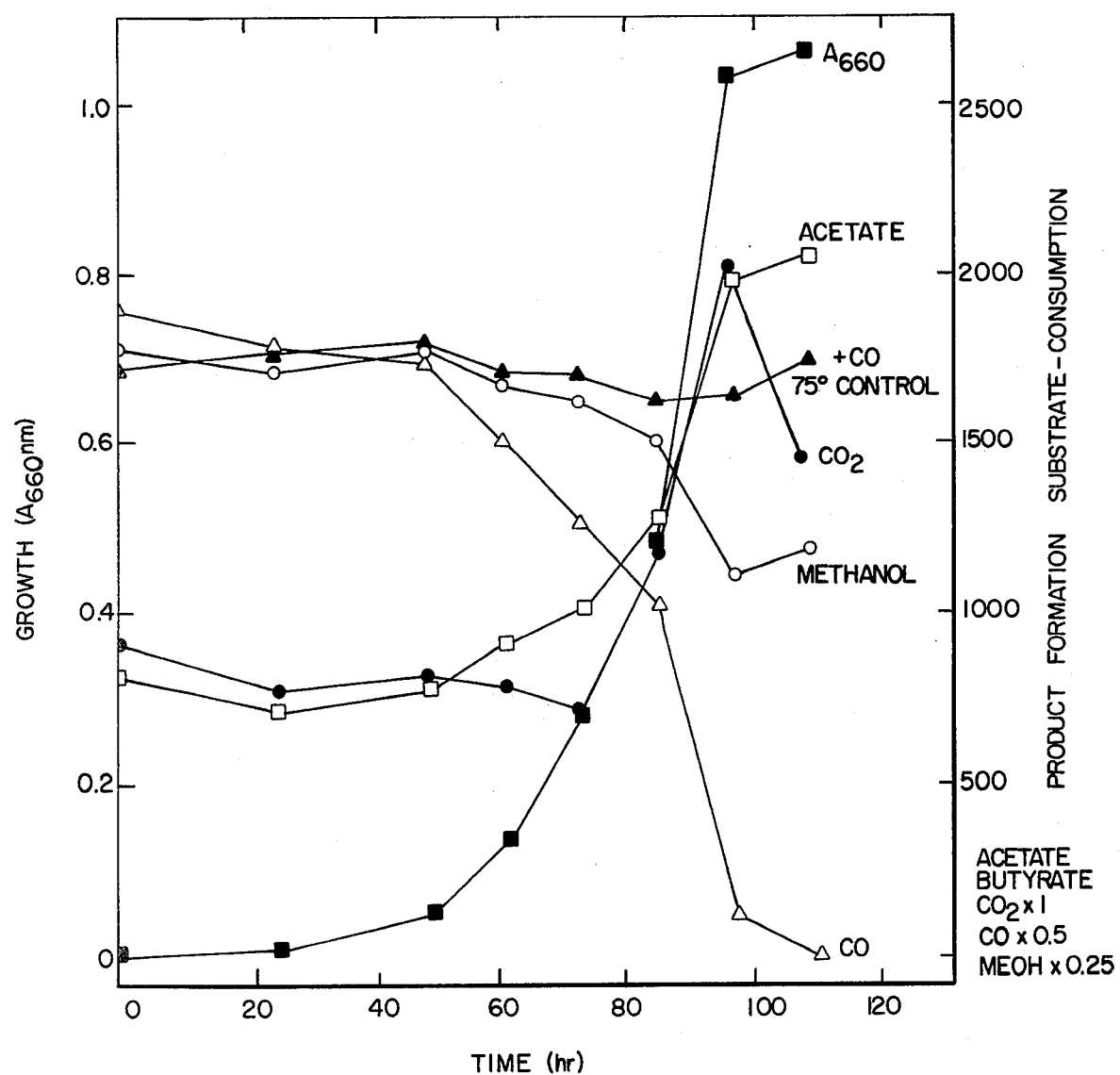
FIG. 3 shows the fermentation parameters of *B. methylotrophicum* adapted to grow on methanol/acetate/-$CO_2$, and CO.

Fermentation of *B. Methylotrophicum* Adapted to Grow on CO-Methanol/Acetate/$CO_2$ A culture of *B. methylotrophicum* adapted to grow on CO-methanol as described in Example 1 was grown in 158 ml. pressure bottles containing 80 ml. of phosphate-buffered mineral medium with 0.05% yeast extract, methanol, acetate, and a 100% CO gas phase at an incubation temperature of 37° C. The fermentation parameters of culture growth under these conditions is shown in FIG. 3.

EXAMPLE 4

Fermentation of *B. Methylotrophicum* on Methanol

The *B. methylotrophicum* was grown in 158 ml. pressure bottles containing 55 ml. of phosphate-buffered mineral medium methanol and 0.05% yeast extract in an $H_2/CO_2$ gas phase at an incubation temperature of 37° C. Samples were analyzed at the beginning and end of growth and the results are reported in Table 3.

TABLE 3

| Methanol Fermentation Parameters of *B. Methylotrophicum* | | | |
|---|---|---|---|
| Substrate-Product Relationships | | | |
| Compound | [Initial] (mM$^a$) | [Final] (mM) | Δ (Total μ Moles) |
| Methanol | 112.4 | 31.1 | −4,472 |

TABLE 3-continued

| Methanol Fermentation Parameters of *B. Methylotrophicum* | | | |
|---|---|---|---|
| $CO_2$ | 18.4 | 3.6 | −814 |
| Acetate | 43.3 | 40.9 | −132 |
| Butyrate | 0 | 21.2 | +1,166 |
| Net Stiochiometry (Total μ Moles): | | | |
| 4,472 Methanol + 814 $CO_2$ + 132 Acetate → 1,166 Butyrate | | | |
| Redox Recovery$^b$: 82% | | | |
| Carbon Recovery: 84% | | | |
| $Y_{MEOH}(G/M)^c$: 7.8 | | | |

$^a$Concentrations of gasses are expressed as the total amount present per liquid volume.

$^b$Redox Recovery = $\frac{\Sigma(\frac{1}{4}O_2 - H)i \times \mu MOL\ Product\ i}{\Sigma(\frac{1}{4}O_2 - H)i \times \mu MOL\ Substrate\ i}$ $^c$The yield was calculated when growth and methanol consumption were proportional.

EXAMPLE 5

Fermentation of *B. Methylotrophicum* (CO strain) on CO

The *B. methylotrophicum* (CO strain) prepared as described in Example 1 was grown in 158 ml pressure bottles containing 52 ml of phosphate-buffered mineral medium with 0.05% yeast extract, and a 100% CO gas phase at an incubation temperature of 37° C. The results are reported in Table 4.

TABLE 4

| CO Fermentation Parameters of *B. Methylotrophicum* (CO-Strain) | | | |
|---|---|---|---|
| Substrate-Product Relationships | | | |
| Compound | [Initial] (mM$^a$) | [Final] (mM) | Δ (Total μ Moles) |
| CO | 95.5 | 4.3 | −4,746 |
| $CO_2$ | 0 | 49.0 | +2,560 |
| Acetate | 0 | 13.1 | + 679 |
| Net Stiochiometry (Total μ Moles): | | | |
| 4,746 CO → 2,560 $CO_2$ + 679 Acetate | | | |
| Redox Recovery$^b$: 83% | | | |
| Carbon Recovery: 108% | | | |
| $Y_{CO}^c$ (G/M): 3.0 | | | |

$^a$Concentrations of gasses are expressed as the total amount present per liquid volume.

$^b$Redox Recovery = $\frac{\Sigma(\frac{1}{4}O_2 - H)i \times MOL\ Product\ i}{\Sigma(\frac{1}{4}O_2 - H)i \times MOL\ Substrate\ i}$ $^c$The yield was calculated when growth and CO were proportional.

EXAMPLE 6

Influence on Fermentation of CO

Pressure tubes (27 ml) containing 10 ml phosphate-buffered mineral medium with 0.05% yeast extract were inoculated with (a) the Marburg strain (tubes with $N_2$); (b) the Co-adapted strains (tubes with CO and an additional substrate); and (c) the CO strain (tubes with CO only). Fermentation parameters were measured at the beginning of growth and in early stationary phase, except for $A_{660}$ which was measured at 8 hour intervals over the course of growth.

The results are reported in Table 5.

TABLE 5

| Influence of CO on the fermentation of glucose, pyruvate, methanol/acetate/$CO_2$, or $H_2/CO_2$ by *B. methylotrophicum*. | | | | | | | | | |
|---|---|---|---|---|---|---|---|---|---|
| Primary Substrate | Gas Phase | Growth Rate ($H^{-1}$) | CO Consumed (%) | Growth (Δ $A_{660}$) | $Y_1^c$ | Substrate$^a$ | Products | | | |
| | | | | | | | Acetate | Butyrate | $CO_2$ | $H_2$ |
| Glucose 50 mM | $N_2$ | 0.117 ± .024 | — | 1.65 ± .07 | 29.1 | | + | + | + | + |
| Glucose 50 mM | CO | 0.101 ± .022 | 14 ± 0 | 1.63 ± .06 | 28.3 | | + | + | + | − |
| Pyruvate 100 mM | $N_2$ | 0.095 ± .002 | — | 1.63 ± .20 | 15.3 | | + | − | + | − |
| Pyruvate 100 mM | CO | 0.066 ± .007 | 35 ± .04 | 1.35 ± .15 | 12.1 | | + | − | + | − |

TABLE 5-continued
Influence of CO on the fermentation of glucose, pyruvate, methanol/acetate/$CO_2$, or $H_2/CO_2$ by B. methylotrophicum.

| Primary Substrate | Gas Phase | Growth Rate ($H^{-1}$) | CO Consumed (%) | Growth ($\Delta A_{660}$) | $Y_1°$ Substrate[a] | Products | | | |
|---|---|---|---|---|---|---|---|---|---|
| | | | | | | Acetate | Butyrate | $CO_2$ | $H_2$ |
| MEOH/AC/$CO_2$[b] | $N_2$ | 0.062 ± .007 | — | 1.19 ± .16 | 6.6 ± .6 | ± | + | − | − |
| MEOH/AC/$CO_2$ | CO | 0.073 ± .005 | 90 ± .05 | 1.06 ± .08 | 14.6 ± .6 | + | ± | + | − |
| $H_2/CO_2$[c] | $N_2$ | 0.038 ± .006 | — | 0.16 ± .04 | 1.4 ± .5 | + | − | − | − |
| $H_2/CO_2$ | CO | 0.038 ± .007 | 95 ± .04 | 0.61 ± .02 | 4.3 ± .7 | + | ± | N.D.[d] | − |
| CO | CO | 0.05 ± .003 | 96 ± .04 | 0.58 ± .08 | 3.3 ± .5 | + | − | + | − |
| $CO_2$ | $N_2$ | 0.00 | — | 0.03 ± .03 | | | | | |

[a] Yields are calculated from a single point in early stationary phase.
[b] MEOH/AC/$CO_2$ = 100 mM Methanol, 50 mM Acetate, + ~ 15% $CO_2$ (% head space).
[c] $H_2/CO_2$ = 2 atmospheres 80% $H_2$/20% $CO_2$; tubes with $H_2CO_2$ had an additional over-pressure of 1 atm $H_2$ or CO.
[d] N.D. = Not determined

EXAMPLE 7

B. Methylotrophicum Growth on Methanol and Acetate under $N_2/CO_2$ gas phase

The Marburg strain was grown under a $N_2/CO_2$ (95:5) gas phase in CBBM medium that contained 0.05% yeast extract, 100 mM methanol, and 50 mM acetate at 37° C. in a 15 liter carboy. The products of the methanol metabolism of the organism are shown in FIG. 1.

In Table 6 the stoichiometries and energetics of methanol and CO fermentation by B. methylotrophicum are recorded.

EXAMPLE 8

B. Methylotrophicum Growth on $H_2$ and CO

Figure 4:
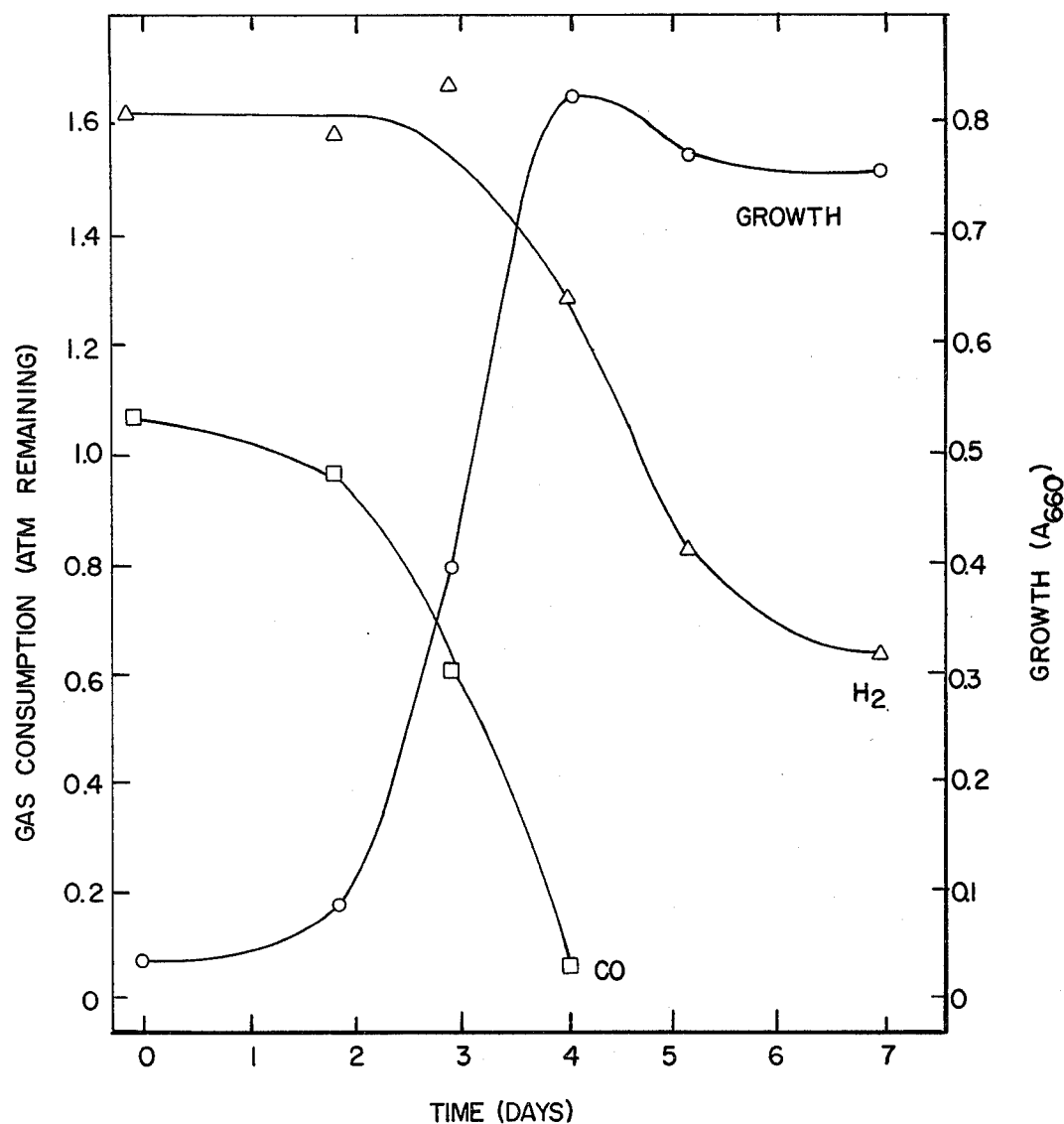
FIG. 4 shows the products of $H_2$ and CO (synthesis gas) metabolism of *B. methylotrophicum*.

The Marburg strain was grown on a 50:50 mixture of $H_2$ and CO in the gas phase under otherwise identical conditions to those in Example 2. The fermentation time course is shown in FIG. 4.

TABLE 6

| | | $\Delta 6°'$ (KCAL) | |
|---|---|---|---|
| | | Per Reaction | Per Mole Methanol or CO |
| I. Fermentation of Methanol to Butyrate | | | |
| (A) Experimental results | 10 MEOH + 1.8 $HCO_3^-$ + 0.2 AC → 2.6 $BUT^-$ | — | — |
| (B) Balanced overall reaction | 10 MEOH + 2 $HCO_3^-$ → 3 $BUT^-$ + $H^+$ + 10 $H_2O$ | −129.9 | −13 |
| (C) Balanced reaction for acetate formation | 4 MEOH + 2 $HCO_3^-$ → 3 $Acetate^-$ + 1 $H^+$ + 4 $H_2O$ | −53.0 | −13.3 |
| (D) Balanced reaction for butyrate formation | 6 MEOH + 3 Acetate → 3 Butyrate + 6 $H_2O$ | −76.6 | −12.8 |
| II. Fermentation of CO to Acetate | | | |
| (A) Experimental results | 4 CO → 2.2 $HCO_3^-$ + 0.6 $AC^-$ | — | — |
| (B) Balanced reaction | 4 CO + 4 $H_2O$ → $HCO_3^-$ + 1 $AC^-$ + $3H^+$ | −39.5 | −9.9 |

EXAMPLE 9

B. Methylotrophicum Growth on Methanol for Corrinoid Production

The Marburg strain was grown under a $N_2/CO_2$ (95:5) gas phase in a medium of the following composition at 37° C. for three days.

| Component | Amount/L |
|---|---|
| Double distilled $H_2O$ | 945 ml |
| $MgCl.6H_2O$ | 0.2 g |
| $CaCl_2.2H_2O$ | 0.1 g |
| $NH_4Cl$ | 7.0 g |
| [a]Trace mineral sln. #2 | 10 ml |
| [b]Vitamin sln. | 5 ml |
| Resazurin solution (0.2%) | 1 ml |
| Yeast extract | 7.0 g |

-continued

| Sodium acetate | | 4.1 g | |
|---|---|---|---|
| Methanol | | 5 ml (125 mM/l) | |
| $Na_2S$ (2.5%) | | 20 ml | |
| (a) | (g/l) | (b) | (g/l) |
| Nitriloacetic acid | 12.8 | Biotin | .002 |
| $FeSO_4.7H_2O$ | 0.1 | Folic acid | .002 |
| $MnCl_2.4H_2O$ | 0.1 | $B_6HCl$ | .01 |
| $COCl_2.6H_2O$ | 0.17 | $B_1HCl$ | .005 |
| $CaCl_2.2H_2O$ | 0.1 | $B_2$ | .005 |
| $ZnCl_2$ | 0.1 | Niacin | .005 |
| $CuCl_2$ | 0.02 | Pantothenic acid | .005 |
| $H_3BO_4$ | 0.01 | $B_{12}$ | .0001 |
| NaCl | 1.0 | PaBA | .005 |
| $Na_2SeO_3$ | 0.017 | Lipoic acid | .005 |
| $NiSO_4.6H_2O$ | 0.026 | | |

The cells were found to contain more than 1% of Vitamin $B_{12}$ on a dry weight basis.

References

1. Quayle, J. R. 1972. The metabolism of one-carbon compounds in microorganisms. Advances in Microbial Physiology 7:118–203.
2. Daniels, L., Fuchs, G., Thauer, R. K., Zeikus, J. G. 1977. Carbon monoxide oxidation by methanogenic bacteria. Journal of Bacteriology 132:118–128.
3. Weimer, P. J., Zeikus, J. G. 1978. One-carbon metabolism in methanogenic bacteria: Cellular characterization and growth of *Methanosarcina barkeri*. Archives of Microbiology 119:49–57.
4. Weimer, P. J., Zeikus, J. G. 1978. Acetate metabolism in *Methanosarcina barkeri*. Archives of Microbiology 119:175–182.
5. Zeikus, J. G., Wolfe, R. S. 1972. *Methanobacterium thermoautotrophicus* sp. n., an anaerobic, autotrophic, extreme thermophile. Journal of Bacteriology 109:707–713.

6. Balch, W. E., Schoberth, S., Tanner, R. S., Wolfe, R. S. 1977. Acetobacterium, a new genus of hydrogen-oxidizing, carbon dioxide-reducing, anaerobic bacteria. International Journal of Systematic Bacteriology 27:355-361.
7. Wieringa, K. T. 1940. The formation of acetic acid from carbon dioxide and hydrogen by anaerobic spore-forming bacteria. Antonie van Leeuwenhoek Journal of Microbiology and Serology 6:251-262.
8. Andreesen, J. R., Gottschalk, G., Schlegel, H. G. 1970, Clostridium formicoaceticum nov. spec. Isolation, description and distinction from Clostridium aceticum. Archiv f',uml/u/ r Mikrobiologie 72:154-174.
9. Fontaine, F. E., Peterson, W. H., McCoy, E., Johnson, M. J., Ritter, G. J. 1942. A new type of glucose fermentation by Clostridium thermoaceticum n. sp. Journal of Bacteriology 43:701-715.
10. Barker, H. A. 1944. Butyribacterium, a new genus of gram-positive nonsporulating anaerobic bacteria of intestinal origin. Journal of Bacteriology 47:301-305.
11. Buchanan, R. E., Gibbons, N. E. 1974. Bergey's manual of determinative bacteriology, 8th ed. Baltimore: Williams & Wilkins.
12. Zeikus, J. G., Hegge, P. W., Anderson, M. A. 1979. Thermoanaerobium brockii gen. nov. and sp. nov. a new chemoorganotrophic, caldoactive, anaerobic bacterium. Archives of Microbiology 122:41-48.
13. Zeikus, J. G., Henning, D. L. 1975. Methanobacterium arbophilicum sp. nov. An obligate anaerobe isolated from wetwood of living trees. Antonie van Leeuwenhoek Journal of Microbiology and Serology 41:543-552.
14. Nelson, D. R., Zeikus, J. G. 1974. Rapid method for the radioisotopic analysis of gaseous products of anaerobic metabolism. Applied and Environmental Microbiology 28:258-261.
15. Zeikus, J. G., Bowen, V. G. 1975. Fine structure of Methanospirillum hungatii. Journal of Bacteriology 121:373-380.
16. Marmur, J. 1961. A procedure for the isolation of deoxyribonucleic acid from microorganisms. Journal of Molecular Biology 3:208-218.
17. De Ley, J. 1970. Reexamination of the association between melting point, buoyant density, and chemical base composition of deoxyribonucleic acid. Journal of Bacteriology 101:738-754.
18. Wells, R. D., Blair, J. E. 1967. Studies on polynucleotides, LXXI. Sedimentation and buoyant density of some DNA-like polymers with repeating nucleotide sequences. Journal of Molecular Biology 27:273-288.
19. Krzycki, J., Zeikus, J. G. 1980. Quantification of Corrinoids in methanogenic bacteria. Current Microbiology 3:243-245.

In summary, the growth of the B. methylotrophicum on methanol (100 mM)/acetate (50 mM) required $CO_2$ and exhibited: a chemical transformation stoichiometry of 10 methanol+$2CO_2$→3 butyrate; a cell yield of 8.2 g/mol methanol; and, a growth rate of 0.067 $h^{-1}$. Cultures adapted to grow on methanol with a CO atmosphere (100%) displayed: a 3-fold increase in growth yield; increased growth rate; no requirement for $CO_2$; and, production of acetate in lieu of butyrate. The maximum rate of CO oxidation displayed by cultures during mixotrophic growth on methanol/CO was 140 mmol/min/mg dry wt. B. methylotrophicum was adapted to grow in batch culture with a 100% CO atmosphere as the sole carbon and energy source. Fermentation parameters for growth on CO were: a chemical transformation stoichiometry of 4CO→2.2 $CO_2$+0.6 acetate; a growth yield of 2.9 g/mol CO; a final $O.D._{660}$ of 0.8; and, a CO-oxidation rate of 260 nmol/min/mg dry wt. B. methylotrophicum grows on a variety of substrates in the presence of one atmosphere CO. Under these conditions, >0.9 atmospheres of CO were consumed during growth on $H_2/CO_2$ or methanol, while <0.4 and <0.2 atmospheres were consumed during growth on pyruvate and glucose respectively. The yield on $H_2/CO_2/CO$ increased greater than two-fold over that observed in the absence of CO. The growth of B. methylotrophicum requires trace substances found in yeast complex in the growth medium and maximum growth on methanol/CO is achieved when the medium contains greater than 10 mM concentrations of acetate.

For larger scale production of cells, acetate or butyrate the B. methylotrophicum can be grown in commercial size fermentations and the cells separated by centrifugation or other conventional techniques.

B. methylotrophicum ATCC 33266 is liable, as are microorganisms generally, to undergo variations and mutations, either spontaneously or under the influence of a mutagen. For example, the many variants of the strain which are obtainable by irradiation with X-rays, gamma rays, ultraviolet light, etc., by monocel isolation, by culture on media containing various chemicals, or by any other mutagenic treatment, as well as the mutants spontaneously derived from the strain, should not be considered to represent any other distinct species but may be utilized for the purposes of this invention.

It will be apparent to those skilled in the art that the present invention is not to be limited by the specific examples described herein. Therefore, it is to be understood that the invention is to be limited only by the claims which follow:

We claim:
1. A process of producing microbial cells usable as a protein source which comprises cultivating the bacterium Butyribacterium methylotrophicum ATCC No. 33266 anaerobically in a medium containing essential minerals and growth factors and a single carbon product selected from carbon monoxide, carbon dioxide and methanol as the main source of assimilable carbon, and separating, then collecting the thus propagated microbial cells of said bacterium.
2. A process of claim 1 in which the medium contains methanol.
3. A process of claim 1 in which the medium contains both methanol and carbon dioxide.
4. A process of claim 1 in which the medium contains a mixture of carbon dioxide and hydrogen.
5. A process of claim 1 in which the medium contains carbon monoxide.
6. The process of claim 5 in which the nutrient medium also contains hydrogen.
7. A process of producing acetic acid which comprises cultivating the bacterium Butyribacterium methylotrophicum ATCC No. 33266 anaerobically in a medium containing essential minerals and growth factors and methanol as the main carbon source in a CO atmosphere, and separating, then collecting the acetic acid.
8. A process of producing butyric acid which comprises cultivating the bacterium Butyribacterium methylotrophicum ATCC No. 33266 anaerobically in a medium containing $CO_2$, acetate methanol and essential minerals and growth factors, and separating, then collecting the butyric acid.

9. A process of producing acetic acid which comprises cultivating a strain of *Butyribacterium methylotrophicum* ATCC No. 33266, which is capable of growing on CO, anaerobically in a medium containing essential minerals and growth factors and CO as the main carbon source and separating, then collecting the acetic acid.

10. A process of producing acetic acid which comprises cultivating the bacterium *Butyribacterium methylotrophicum* ATCC No. 33266 in a medium containing essential minerals and growth factors and a mixture of $CO_2$ and $H_2$ as the main carbon source in a CO atmosphere and separating and collecting the acetic acid.

11. A process of producing acetic acid which comprises cultivating the bacterium *Butyribacterium methylotrophicum* ATCC No. 33266 anaerobically in a nutrient medium containing essential minerals and growth factors and a mixture of CO and $H_2$ as the main carbon source and separating and collecting the acetic acid.

12. A biologically pure culture of *Butyribacterium methylotrophicum* ATCC 33266, said culture being capable of growing on a single carbon product selected from carbon monoxide, carbon dioxide and methanol as the main source of assimilable carbon and producing acetic or butyric acid in recoverable quantities.

13. A biologically pure culture of *Butyribacterium methylotrophicum* ATCC 33266 and a medium consisting essentially of essential minerals and growth factors and a single carbon product selected from carbon monoxide, carbon dioxide and methanol as the main source of assimilable carbon, said culture when maintained at anaerobic fermentation conditions being capable of producing acetic or butyric acid in recoverable quantity.

* * * * *